United States Patent
Avcioglu (10) Patent No.: US 11,179,188 B2
(45) Date of Patent: Nov. 23, 2021

(54) SURGICAL DEVICE WITH FUNCTIONAL DEVICE

(71) Applicant: OLYMPUS WINTER & IBE GMBH, Hamburg (DE)

(72) Inventor: Erdinc Avcioglu, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 458 days.

(21) Appl. No.: 15/436,125

(22) Filed: Feb. 17, 2017

(65) Prior Publication Data

US 2017/0231682 A1 Aug. 17, 2017

(30) Foreign Application Priority Data

Feb. 17, 2016 (DE) ...................... 10 2016 202 456.6

(51) Int. Cl.
*A61B 18/12* (2006.01)
*A61B 18/00* (2006.01)
(Continued)

(52) U.S. Cl.
CPC .. *A61B 18/1206* (2013.01); *A61B 17/320068* (2013.01); *A61B 18/00* (2013.01);
(Continued)

(58) Field of Classification Search
CPC .... A61N 2007/0004; A61N 2007/0008; A61N 2007/0017; A61N 2007/0034; A61N 2007/0039; A61N 2007/0043; A61N 2007/0047; A61B 18/1206; A61B 2018/00023; A61B 2018/00702; A61B 2018/0094
(Continued)

(56) References Cited

U.S. PATENT DOCUMENTS 5,108,389 A * 4/1992 Cosmescu ............... A61B 18/20
128/908
6,945,981 B2 * 9/2005 Donofrio ....... A61B 17/320068
606/169

(Continued)

FOREIGN PATENT DOCUMENTS

CN 204707112 U 10/2015
DE 2712734 A1 9/1978
(Continued)

OTHER PUBLICATIONS

US 11,064,983 B2, 07/2021, Bucina (withdrawn)*
(Continued)

*Primary Examiner* — Eric D. Bertram
(74) *Attorney, Agent, or Firm* — Oliff PLC (57) ABSTRACT

A surgical device including a surgical generator configured to provide energy for an energy based surgical instrument; a functional device configured to provide a function in its activated state; a switch for activating and deactivating the surgical generator a capacitive sensor including at least one measuring electrode that is arranged at the switch, wherein the capacitive sensor is configured to measure a capacity change or a capacity at the measuring electrode and activate or deactivate the functional device as a function of a measured capacity change or capacity.

13 Claims, 7 Drawing Sheets

(51) Int. Cl.
*H03K 17/96* (2006.01)
*A61B 17/32* (2006.01)
*A61B 18/20* (2006.01)

(52) U.S. Cl.
CPC ........... *A61B 18/12* (2013.01); *H03K 17/962* (2013.01); *A61B 18/20* (2013.01); *A61B 2018/00023* (2013.01); *A61B 2018/0094* (2013.01); *A61B 2018/00589* (2013.01); *A61B 2018/00601* (2013.01); *A61B 2018/00607* (2013.01); *A61B 2018/00666* (2013.01); *A61B 2018/00708* (2013.01); *A61B 2018/00827* (2013.01); *A61B 2218/008* (2013.01); *H03K 2017/9613* (2013.01); *H03K 2017/9615* (2013.01); *H03K 2217/96078* (2013.01)

(58) Field of Classification Search
USPC ............................... 606/2–19, 169; 424/677
See application file for complete search history.

(56) References Cited

U.S. PATENT DOCUMENTS

| | | | | |
|---|---|---|---|---|
| 10,575,892 | B2* | 3/2020 | Danziger | A61B 90/98 |
| 10,595,930 | B2* | 3/2020 | Scheib | A61B 17/068 |
| 2004/0000438 | A1* | 1/2004 | Stree | G01G 3/1412 |
| | | | | 177/178 |
| 2010/0069940 | A1* | 3/2010 | Miller | A61B 17/320068 |
| | | | | 606/169 |
| 2011/0169506 | A1 | 7/2011 | Aubauer et al. | |
| 2012/0203213 | A1* | 8/2012 | Kimball | A61B 17/320068 |
| | | | | 606/1 |
| 2016/0211842 | A1* | 7/2016 | Chang | H03K 17/962 |
| 2016/0278874 | A1* | 9/2016 | Fleenor | A61B 90/30 |
| 2017/0172614 | A1* | 6/2017 | Scheib | A61B 17/320092 |
| 2017/0194115 | A1* | 7/2017 | Blus | H01H 13/70 |
| 2017/0215936 | A1* | 8/2017 | Wallace | A61B 18/082 |

FOREIGN PATENT DOCUMENTS

| | | |
|---|---|---|
| DE | 602004012972 T2 | 6/2009 |
| DE | 202010015327 U1 | 1/2011 |
| DE | 102009042438 A1 | 3/2011 |
| DE | 202010018025 U1 | 11/2013 |
| EP | 0017318 A1 | 10/1980 |
| WO | 2011/080308 A1 | 7/2011 |

OTHER PUBLICATIONS

Adrian Freed, E-Field (Capacitive) Sensing Foot Switch, cnmat.berkeley.edu/content/e-field-capacitive-sensing-food-switch, May 14, 2008 (Year: 2008).*

Jun. 30, 2017 Extended Search Report issued in European Patent Application No. 17156567.4.

Jul. 20, 2020 Office Action issued in European Patent Application No. 17156567.4.

* cited by examiner

SURGICAL DEVICE WITH FUNCTIONAL DEVICE

This application claims the benefit of DE 10 2016 202 456.6, filed on Feb. 17, 2016. The disclosure of the prior application is hereby incorporated by reference herein in its entirety.

The invention relates to a surgical device with a surgical generator, a switch, a functional device in particular a smoke extractor and a capacitive sensor. The invention furthermore relates to a capacitive measuring device attachable to a switch, in particular a foil with a measuring electrode. The invention furthermore relates to a method for essentially synchronous automatic activating and deactivating of a functional device, in particular a smoke-gas extraction device and a surgical generator of a surgical device.

Surgical devices with functional devices like for example smoke, gas extraction devices are known. Surgical devices can thus include one or plural function devices which take over particular function upon activation such as e.g. extracting smoke-gas. Surgical devices of this type are typically used in operating rooms or treatment rooms when treating patients. When cutting and coagulating tissue with energy based surgical instruments, for example high frequency surgical instruments, tissue is evaporated and body fluid is vaporized which generates a smoke-gas which includes the vaporized tissue and the vaporized body fluid in a form of smoke-gas particles. This smoke-gas can make it difficult to see the tissue to be treated and can cause health risks. Therefore smoke-gas extraction devices are being used in order to remove the smoke-gas from the operating room. Another function device can be for example an illumination device such as e.g. a lamp which can improve visibility of the tissue to be treated upon activation.

Different methods and devices are used for surgical smoke-gas extraction in order to activate the smoke-gas extraction device only when it is needed. The smoke-gas extraction device can be activated manually or automatically. For manual activation the surgical device can include a switch which can be arranged for example at the surgical instrument or which can be connected with the surgical instrument as a foot switch. During manual activation the smoke-gas extraction device is activated either by manual activating at the switch at the surgical instrument or by manual activating of the foot switch. Various devices and methods are used for automatic activating in order to activate the surgical generator, for example an electrical surgical generator and the smoke-gas extraction device synchronously.

In a first known surgical device an electrical current flow through a cable which connects the surgical generator with the surgical instrument is detected inductively for automated activating of the smoke-gas extraction device. The electrical current flow can be detected for example directly in the surgical instrument or by a detector arranged at the cable. In response to a detected electrical current flow through the cable a signal can be transmitted from the surgical instrument or from the detector to the smoke-gas extraction device in order to activate the smoke-gas extraction device. When no current flow is detected anymore a signal for deactivating the smoke-gas detection device can be transmitted.

In a second known surgical device the fact is used that surgical generators typically emit acoustic signals for example tones that can be differentiate from each other when activating the so called "cut" and "coagulate" function. The surgical device includes an acoustic sensor which activates the smoke-gas extraction device when a predetermined tone is detected. Deactivating the smoke-gas extraction device can be performed when the acoustic sensor detects a respective tone that is emitted by the surgical generator.

In a third known surgical device the surgical generator is connected directly with the smoke-gas extraction device, for example in that the power plug of the surgical generator is directly connected to the smoke-gas extraction device. The smoke-gas extraction device can measure a current draw of the surgical generator and upon corresponding calibration activation of the smoke-gas extraction generator can be synchronized with the activation of the surgical generator. In this case the smoke-gas extraction device can be activated automatically when the surgical generator is activated.

It is an object of the invention to provide an improved surgical device with a functional device.

The object is achieved with a surgical device with a surgical generator, a functional device, a switch and a capacitive sensor. The surgical generator is configured to provide energy for an energy based surgical instrument. In its activated state the functional device is configured to provide a function. The switch is used for activating and deactivating the surgical generator. The capacitive sensor includes at least one measuring electrode. The measuring electrode is arranged at the switch. The capacitive sensor is configured to measure a capacity change or a capacity at the measuring electrode and to activate or deactivate the functional device as a function of the measured capacity change or capacity.

Advantageously the functional device is a smoke-gas extraction device that is configured to extract smoke-gas in its activated state. The function device can also be an illumination device that is configured to provide a special light in its activated state which improves visibility. Furthermore the function device can include a blinking light that is configured to indicate to the user of the surgical device that the functional device was activated and/or that the surgical generator is activated when the switch is activated further. The blinking light can for example have a warning function. Furthermore the functional device can form a control for a charger or can include the charger wherein the charger is configured to charge an energy source for example of an energy based surgical device in its activated state. Furthermore the function device can be a video recording device for recording video data or photographic or it can include a video recording device. Furthermore the functional device can include an audio recording device for recording audio data, in particular voice data or it can include an audio recording device. Furthermore the function device can be a temperature control device that is configured to heat and/or cool an electrosurgical instrument and/or an endoscope. The functional device can also include a temperature control device of this type. The functional device can furthermore be a control device which is configured to control additional external devices, such as e.g. a computer, mobile phone, a tablet computer or similar in its activated state. The control device can for example also be configured to control a pump for example for coolant supply. Plural function devices can also be activated using the capacitive sensor.

When the smoke-gas extraction device is activated it sucks in a gas and is used in particular to extract smoke-gas. When the surgical generator is activated it provides energy that can be used in particular for operating an energy based surgical instrument.

The capacitive sensor can measure a capacity change at the measuring electrode, the capacity at the measuring electrode or a capacity change and a capacity at the measuring electrode and can activate or deactivate the functional device as a function thereof. The capacitive sensor can be for example a contact sensor, a proximity sensor or a similar capacitive sensor or it can include one or plural sensors of this type. The capacity at the measuring electrode is a function of how far a surface is away from the measuring electrode or whether a surface is placed on the measuring electrode. A surface can be for example a surface of an object like the surface of a finger for a hand switch or the surface of a foot for a foot switch. The surface of the foot and the surface of the measuring electrode essentially form two opposite surfaces of a capacitor. A capacity of the capacitor depends from various factors, in particular the distance of the surfaces. The capacitive sensor can be set up so that it transmits an activation signal for activating or a deactivation signal for deactivating the functional device if for example a predetermined threshold value of capacity and/or capacity change is exceeded or undercut.

The capacitive sensor furthermore includes control logic which generates a control signal for activating or deactivating the functional device from a measurement value generated by the measuring electrode.

The surgical device facilitates essentially synchronous activating of the surgical generator and the functional device. Advantageously activating the functional device is performed upon or shortly after activating the surgical generator. For this purpose for example a predetermined threshold value for the capacity and/or the capacity change can defined so that the capacitive sensor activates the functional device when the switch is activated on which the measuring electrode of the capacitive sensor is arranged. Thus initially the functional device and immediately thereafter or at the same time or synchronously the surgical generator is activated. The surgical generator can be connected with an energy based surgical instrument, for example an ultrasound surgical instrument, a laser surgical instrument, an electrode surgical instrument or a similar based surgical instrument. The surgical instrument is supplied with power by the surgical generator so that the surgical generator can be used to cut and/or coagulate tissue. Using the energy based surgical instrument for treating tissue generates smoke-gas. This smoke-gas can be extracted for example by a functional device configured as a smoke-gas extraction device.

The smoke-gas extraction device can include for example a pump which is connected through a lumen of a conduit such as e.g. of a hose with the energy based surgical instrument. The energy based surgical instrument can include an inlet opening which is advantageously arranged proximal to the cutting and/or coagulation tool of the energy based surgical instrument and connected with the lumen of the conduit. The smoke-gas can be extracted through the inlet opening and the lumen of the conduit which facilitates efficient extraction of the smoke-gas directly adjacent to its location of generation.

The invention is based on the finding that the known devices and methods for activating and deactivating the surgical generator and a functional device have numerous disadvantages. The invention does not have these disadvantages or can at least mitigate these disadvantages. Compared to manual activation the invention facilitates omitting additional actions which are required when manually activating the surgical generator and the functional device. For example in the case of a manual activation the functional device has to be manually activated in a first step and in a second step the surgical generator has to be manually activated. The invention facilitates almost synchronous activation of the function device and/or the surgical generator without an additional method step. This improves ease of use of the surgical device. Automatic activation by the first known surgical device which activates a functional device configured as a smoke-gas extraction device when a current flow through the cable between the energy based surgical instrument and the surgical generator is inductively detected does not work reliably for shield cables, so that an automatic activation of the functional device fails in about half of all cases. Compared to that the invention also facilitates using shielded cables. Automatic activating using the second known surgical device which detects acoustic signals like tones with an acoustic sensor in order to activate a functional device as a smoke-gas extraction device in response to the detection requires that the acoustic signals, for example tones of different surgical generators are identical. This is typically not the case for different surgical generators. Therefore surgical generators solely tuned to the acoustic sensor can be used in the second known surgical device. Furthermore there is a problem in this case that interfering sounds can impede the detection of the acoustic signal. The third known surgical device where the power plug of the surgical generator is directly connected to a functional device configured as a smoke extraction device requires that the surgical generator includes a cold unit plug standardized according to IEC 320 in order to be compatible. Furthermore the surgical generator has to operate in a particular power range in order to be compatible with the functional device. Therefore not all surgical generators can be used in the third known surgical device. In particular when the surgical device includes plural functional devices it can be difficult to keep them compatible with each other. All known surgical devices and methods for activating the surgical device have to be compatible to the surgical generator with the functional device.

It is an aspect of the invention to that compatibility of the surgical generator with the functional device is not required since the surgical generator can be activated and deactivated by the switch and the functional device can be activated and deactivated by the capacitive sensor. The surgical generator and the functional device can therefore operate in different power ranges and do not have to be calibrated to each other. Furthermore no compatibility requirements have to be complied with by the surgical generator, the energy based surgical instrument and the switch in order to couple and use them together with the functional device and the surgical device. Almost synchronous activating of the functional device when the surgical generator is activated facilitates reducing energy consumption since the functional device does not have to be operated permanently. Furthermore synchronous automatic activation of a functional device configured as a smoke-gas extraction device facilitates effectively extracting the smoke-gas. Furthermore a noise volume of the surgical device can be reduced since the smoke-gas extraction device essentially only has to be active when the smoke-gas is being generated, this means when the surgical generator is activated and supplies an energy based surgical instrument with energy. Also a risk of suctioning an opening of the conduit of the smoke-gas extraction device at a body can be reduced. Furthermore the switch can be insertable into an autoclave and can therefore be arranged in the sterile field.

The surgical generator and/or the functional device can be configured to be switched on initially in order to be put into a stand-by mode. Activating and deactivating the functional device is performed in this case in a ready to operate condition. This facilitates faster reaction times and a reduction of energy consumption.

In an advantageous embodiment of the surgical device the measuring electrode is arranged at the switch and the capacitive sensor is adjusted so that activating the surgical generator also causes an activation of the functional device. Advantageously the measuring electrode is glued onto the switch so that actuating the switch also leads to touching the capacitive, for example a contact sensor. This assures that the functional device is always activated when the surgical generator is activated.

The measuring electrode is advantageously additionally or alternatively arranged at the switch and the capacitive sensor is advantageously additionally or alternatively adjusted so that deactivating the functional device also causes deactivating the surgical generator. In case of a functional device configured as a smoke-gas extraction device this assures that deactivating the smoke-gas extraction device also deactivates the surgical generator. This prevents that smoke-gas is generated by the surgical device while the smoke-gas generator is deactivated.

In one embodiment plural measuring electrodes for example two measuring electrodes of the capacitive sensor can be arranged at the switch and the capacitive sensor can be configured so that it only activates the functional device when a capacity change and/or capacity is measured at the two measuring electrodes which capacity change and/or capacity exceeds a predetermined threshold value. In this embodiment the surgical generator can be activated without activating the functional device when for example the threshold value of the capacity change and/or capacity is only exceeded for one of the two measuring electrodes. This would be the case for example for a foot switch with a respective measuring electrode per foot when only one foot is placed on a measuring electrode.

In a particularly advantageous embodiment of the surgical device the capacitive sensor is configured so that activating or deactivating the functional device is essentially performed synchronously with activating or deactivating the surgical generator. For this purpose the capacitive sensor is advantageously arranged on the switch such that the functional device is activated during or directly before activating the switch for activating the surgical generator and in turn the functional device is deactivated during or directly after the deactivating the surgical generator.

The surgical device advantageously includes a capacitive measuring device that is attachable to the switch. The capacitive measuring device is advantageously configured as a foil. Alternatively or additionally the capacitive measuring device can include one or plural foils and/or wires. Particularly advantageous the capacitive measuring device includes the measuring electrode of the capacitive sensor. The surgical device can also include plural capacitive measuring devices that are attachable to the switch, e.g. foils. The measuring devices can include one or plural measuring electrodes of the capacitive sensor. Advantageously the capacitive measuring device or the capacitive measuring devices are attached to the switch. Particularly advantageously the capacitive measuring device or the capacitive measuring devices are glued to the switch so that they are essentially remove able again without residuals. This facilitates to replace the capacitive measuring device, in particular configured as a foil, after single use so that disposable foils can be used. Using disposable foils facilitates reducing a germ loading of the surgical device. In particular the switch of the surgical device is advantageously insertable into an autoclave so that removing the foil for putting the switch into the autoclave facilitates substantial de-germination. In this case, after being put into the autoclave and before further use of the surgical device a new capacitive measuring device, in particular configured as a foil, is attached at the switch, for example glued onto the switch.

The measuring electrode is advantageously applied as a metal oxide coating onto the capacitive measuring device. Alternatively the measuring electrode can also be mounted on the capacitive measuring device, for example the measuring electrode can be glued to the capacitive measuring device.

In an advantageous embodiment the capacitive sensor includes measuring electronics which form for example the control logic of the capacitive sensor or can be connected therewith. The measuring electronics are advantageously configured to measure the capacity change or the capacity at the measuring electrode. The measuring electronics of the capacitive sensor can be arranged in the functional device. Advantageously the measuring electronics of the capacitive sensor are connected with the measuring electrode through a cable. The measuring electrode and the cable are advantageously useable only once in this case. Alternatively the capacitive sensor can also be connected with the functional device through a cable. In this case the measuring electronics of the capacitive sensor are arranged at the cable between the measuring electrode and the functional device. In this embodiment the cable advantageously includes a measuring electronics housing. The measuring electronics housing is used for receiving the measuring electronics. Advantageously the measuring electrode is useable only once and the cable with the measuring electronic made in the measuring electronics housing is reuseable. In this case the measuring electronics can be arranged proximal to the measuring electrode. A shorter distance between the measuring electrode and the measuring electronics facilitates a reduction of failure propensity and interferences.

In another embodiment the capacitive sensor includes at least one shield electrode. The shield electrode is advantageously arranged proximal to the measuring electrode and configured to shield an in homogenous edge portion of the electrical field against the measuring electrode. This facilitates a more homogeneous electrical measuring field. The shield electrode can be arranged for example about the measuring electrode.

In a particularly advantageous embodiment the switch is a foot switch. The foot switch is configured to be actuated by one foot or plural feet and can be a foot pedal or similar for example. The foot switch can also include plural foot pedals for example two foot pedals. In this case the switch can be configured so that the surgical generator is only activated when both foot pedals are actuated simultaneously. The switch can also be configured so that the surgical generator is activated when one of the two foot pedals is actuated.

Particularly advantageously the surgical device includes an energy based surgical instrument. The energy based surgical instrument is advantageously configured to cut and/or coagulate tissue. The energy based surgical instrument can be for example an ultra sound surgical instrument, a laser surgical instrument, an electro surgical instrument or another energy based surgical instrument. The electrosurgical instrument includes at least one electrode and is configured to be operated by a high frequency alternating voltage in order to cut and/or coagulate tissue. Cutting the tissue and also coagulating the tissue leads to a development of smoke-gas. The smoke-gas can be extracted for example using a functional device configured as a smoke-gas extraction device. Thus a visibility of the tissue to be treated can be improved. Furthermore the smoke-gas can also pose a health risk for a patient treated with the surgical device or for a physician using the surgical device. Removing the smoke-gas using the smoke-gas extraction device facilitates reducing the health risk of the user and of the patient. By activating the smoke-gas extraction device when the surgical generator is activated it can be assured that the health risk is minimized.

The invention furthermore relates to a capacitive measuring device for the surgical device which is attachable to the switch. The capacitive measuring device includes a measuring electrode. The measuring electrode forms at least a portion of a capacitive sensor when installed into the surgical device. The measuring electrode is furthermore connected in an installed condition through a cable with measuring electronics of the capacitive sensor. The capacitive sensor is configured to measure a capacity change or a capacity at the measuring electrode and to provide an output signal as a function of the measured capacity change or capacity. Advantageously the output signal is an activation signal for activating a functional device for example a smoke-gas extraction device or deactivation signal for deactivating the functional device for example the smoke-gas extraction device. The capacitive measuring device can be useable only once or it can be re-useable. The capacitive measuring device is configured so that it is useable in known surgical devices, this means the surgical devices can be retrofitted with the capacitive measuring device in order to facilitate a synchronous automatic activation of the functional device, for example of the smoke-gas extraction device and of the surgical generator. The capacitive measuring device is advantageously configured as a foil. Alternatively or additionally the capacitive measuring device can include a foil and/or one or plural wires. The invention also relates to a switch for a surgical device where a capacitive measuring device, for example a foil with a measuring electrode is attached. The switch can be for example a foot switch such as e.g. a foot pedal.

The invention furthermore relates to a method for essentially synchronous automatic activating and deactivating of a functional device and a surgical generator of a surgical device. The surgical device includes a switch for activating and deactivating the surgical generator and a measuring electrode of a capacitive sensor arranged at the switch for activating and deactivating the functional device. The method includes the steps:

Placing an object onto the measuring electrode of the capacitive sensor;
Measuring a capacity or capacity change at the measuring electrode with the capacitive sensor,
Automatic activating or automatic deactivating of the functional device when a predetermined threshold value of a capacity change or a capacity is exceeded, and
Actuating the switch for actuating the surgical generator or removing the object from the switch for deactivating the surgical generator.

Advantageously the threshold value of the capacity change of capacity is selected so that the functional device is actuated when the switch is activated and the functional device is deactivated when the object is removed from the capacity sensor. The object can be for example a hand, a finger a foot or another interactive object of a user a threshold value of the capacity change or capacity thus selected provides that essentially synchronous activating and deactivating of the surgical generator and the functional device is performed.

The invention furthermore relates to a use of the surgical device according to the invention.

The invention is now described in more detail with reference to embodiments that are schematically illustrated in the figures, wherein.

Figure 1:
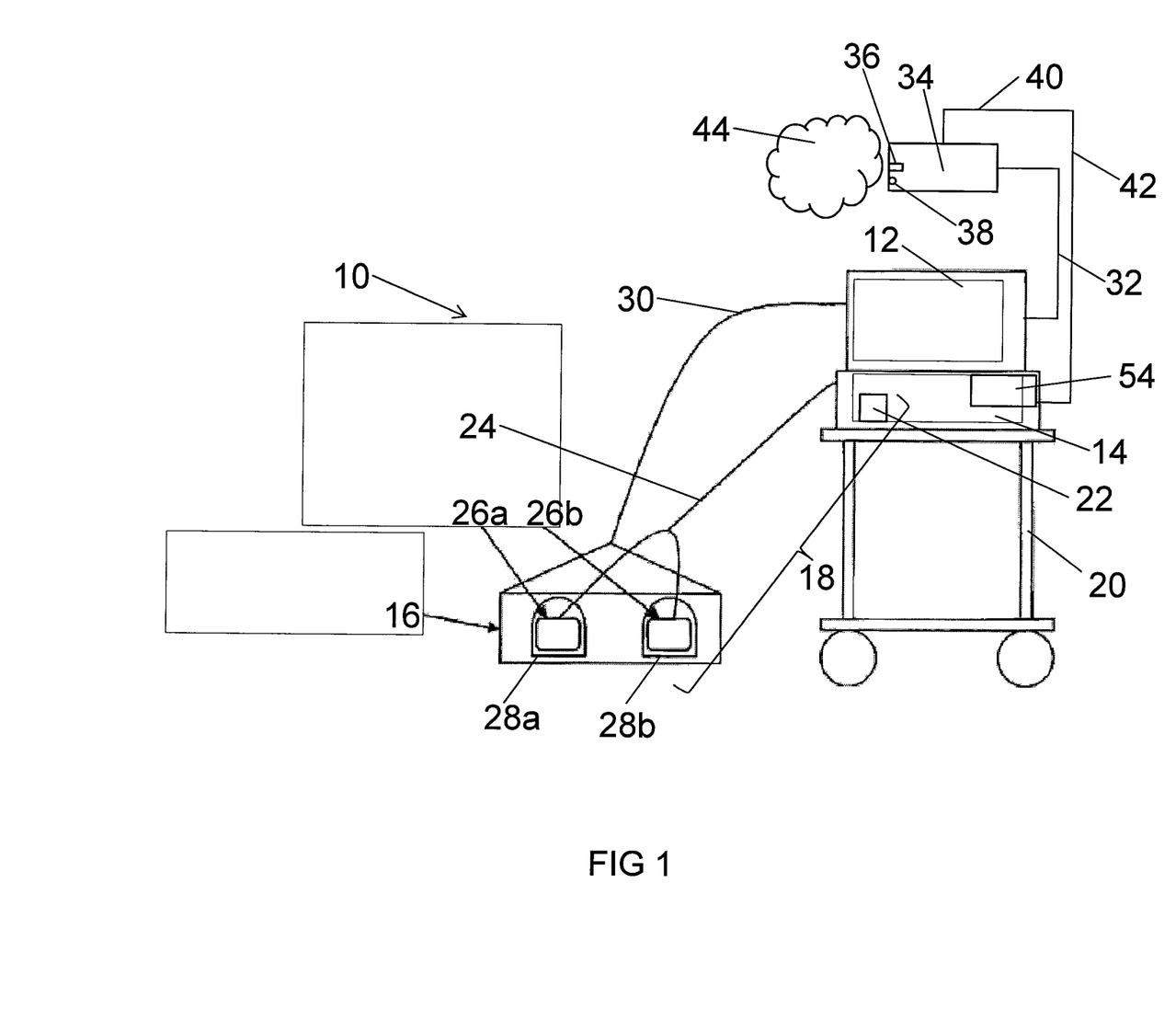
FIG. 1 illustrates a schematic view of a first embodiment of a surgical device.

FIG. 1 illustrates an embodiment of a surgical device 10. The surgical device 10 includes a surgical generator 12, a smoke-gas extraction device 14, a foot switch 16 and a capacitive sensor 18. In this embodiment a functional device configured as a smoke-gas extraction device 14 is used.

The surgical generator 12 and the smoke-gas extraction device 14 are placed on a transport cart 20. Also the foot switch 16 can be placed onto the transport cart 20. This facilitates bringing the surgical device 10 to it location of use, for example a body of a patient. The surgical device 10 can be used in particular for treating body tissue, for example cutting and/or coagulating of the tissue.

Figure 7:
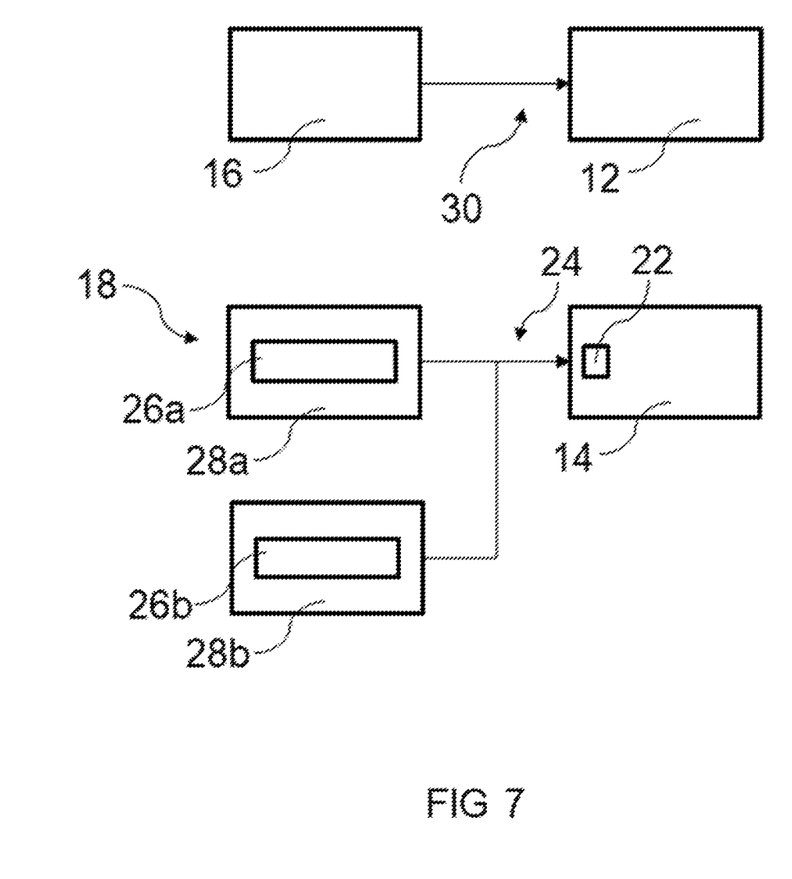
FIG. 7 illustrates a block diagram showing activation/deactivation of the surgical generator by a switch, and activation/deactivation of a functional device by a capacitive sensor.

As shown in FIGS. 1 and 7, the foot switch 16 is connected through a switch cable 30 with the surgical generator 12, and is used for activating and deactivating the surgical generator 12. The foot switch 16 can be actuated for example by two feet or one foot so that a signal is sent through the switch cable 30 the activate the surgical generator 12. When the foot is taken off the foot switch 16 the surgical generator 12 id deactivated. Alternatively also another type of switch, for example a hand switch can be used (not shown).

The capacitive sensor 18 shown in FIGS. 1 and 7 has measuring electronics 22 and two measuring electrodes (26a, 26b) which are connected with each other through the sensor cable 24. In this embodiment the smoke-gas extraction device 14 includes measuring electronics 22 of the capacitive sensor 18. The measuring electrodes 26a, 26b form a respective portion of coils (28a, 28b) which are glued onto the foot switch 16. Alternatively the measuring electrodes 26a, 26b can also be glued onto the foils 28a, 28b. The measuring electrodes 26a, 26b can be applied to the foils 28a, 28b for example as a metal oxide coating. The foils 28a and 28b are in this case disposable foils which are easily remove able from the foot switch 16. This facilitates removing the foils 28a, 28b for treating the foot switch 16 in an autoclave. After autoclave treatment new disposable foils 28a and 28b with electrodes 26a and 26b can be glued onto the foot switch 16. In this embodiment also the sensor cable 24 is a disposable cable so that measuring electrodes 26a, 26b and foils 28a and 28b and the sensor cable 24 are replaced before each use of the surgical device 10 in order to assure that the surgical device 10 is sterile. Alternatively the foils 28a and 28b, measuring electrodes 26a and 26b and the sensor cable 24 can also be reuse able, for example when a very sterile environment is not required.

Instead of foils for example also a wire or a wire mesh or plural wires or other capacitive measuring devices can be used. The wire or the wires can be applied for example or clamped down. In this embodiment the foil is used as a capacitive measuring device.

The capacitive sensor 18 can measure a capacity and a capacity change at the measuring electrodes 26a and 26b. As shown in FIG. 7, the capacitive sensor 18 is configured to activate or deactivate the smoke-gas extraction device 14 as a function of the measured capacity change or capacity. When a foot is placed on one of the measuring electrodes 26a, or 26b the measuring electronics 22 of the capacitive sensor 18 measure the capacity change and the capacity at the measuring electrode 26a or 26b so that the measuring electronics transmit an activation signal to the smoke-gas extraction device 14 to activate the smoke-gas extraction device. For this purpose a threshold value of the capacity change and the capacity in the measuring electronics 22 are defined. When the measuring valve of the capacity change exceeds the threshold value of the capacity change the activation signal is transmitted to the smoke-gas extraction device 14 and the smoke-gas extraction device 14 is activated. Alternatively the measuring electronics 22 can also be configured so that the activation signal is transmitted to the smoke-gas extraction device 14 when the threshold value of the capacity is exceeded so that the smoke-gas extraction device is activated. Furthermore the measuring electronics 22 can also be configured so that the activation signal is only transmitted to the smoke-gas extraction device 14 when the threshold value of the capacity change as well as the threshold value of the capacity is exceeded. When the foot is removed from the measuring electrode 26a, 26b and no foot is placed any more onto one of the measuring electrodes 26a, 26b the smoke-gas extraction device 14 is deactivated by the measuring electronics 22 of the capacitive sensor 18. For this purpose a deactivation signal can be transmitted to the smoke-gas extraction device 14 in order to deactivate it. By gluing the measuring electrodes 26a, 26b onto the foot switch 16 it is assured that activating the foot switch 16 for activating the surgical generator 12 also activates the smoke-gas extraction device 14 automatically and deactivating the smoke-gas extraction device 14 also deactivates the surgical generator 12. This facilitates almost synchronous activating and deactivating of the smoke-gas extraction device 14 and the surgical generator 12.

The capacitive sensor 18 in this embodiment is a contact sensor. Alternatively the capacitive sensor 18 can be for example also a proximity sensor. A capacity change is measured by the capacitive sensor 18 in particular when an object for example a foot, a hand or similar approaches the measuring electrode 26a, 26b of the capacitive sensor in order to be placed on to the capacitive sensor. The approaching object represents a surface that moves relative to the surface of the measuring electrode 26a or 26b. Together the measuring electrode 26a or 26b and the approaching object form two plates of a capacitor. In particular due to the distance change of the surface of the object relative to the surface of the measuring electrode 26a or 26b the capacity of the capacitor formed from the measuring electrode 26a or 26b and the object changes. The measuring electronics 22 of the capacitive sensor 18 measure the capacity change and/or the capacity at the measuring electrode 26a or 26b and activates or deactivates the smoke-gas extraction device 14 as a function of the capacity change and/or the capacity. Thus, as shown in FIG. 7, the switch 16 is designed to activate or deactivate the surgical generator, and the capacitive sensor 18 functions as a switch to activate and deactivate the smoke-gas extraction device 14.

Figure 3:
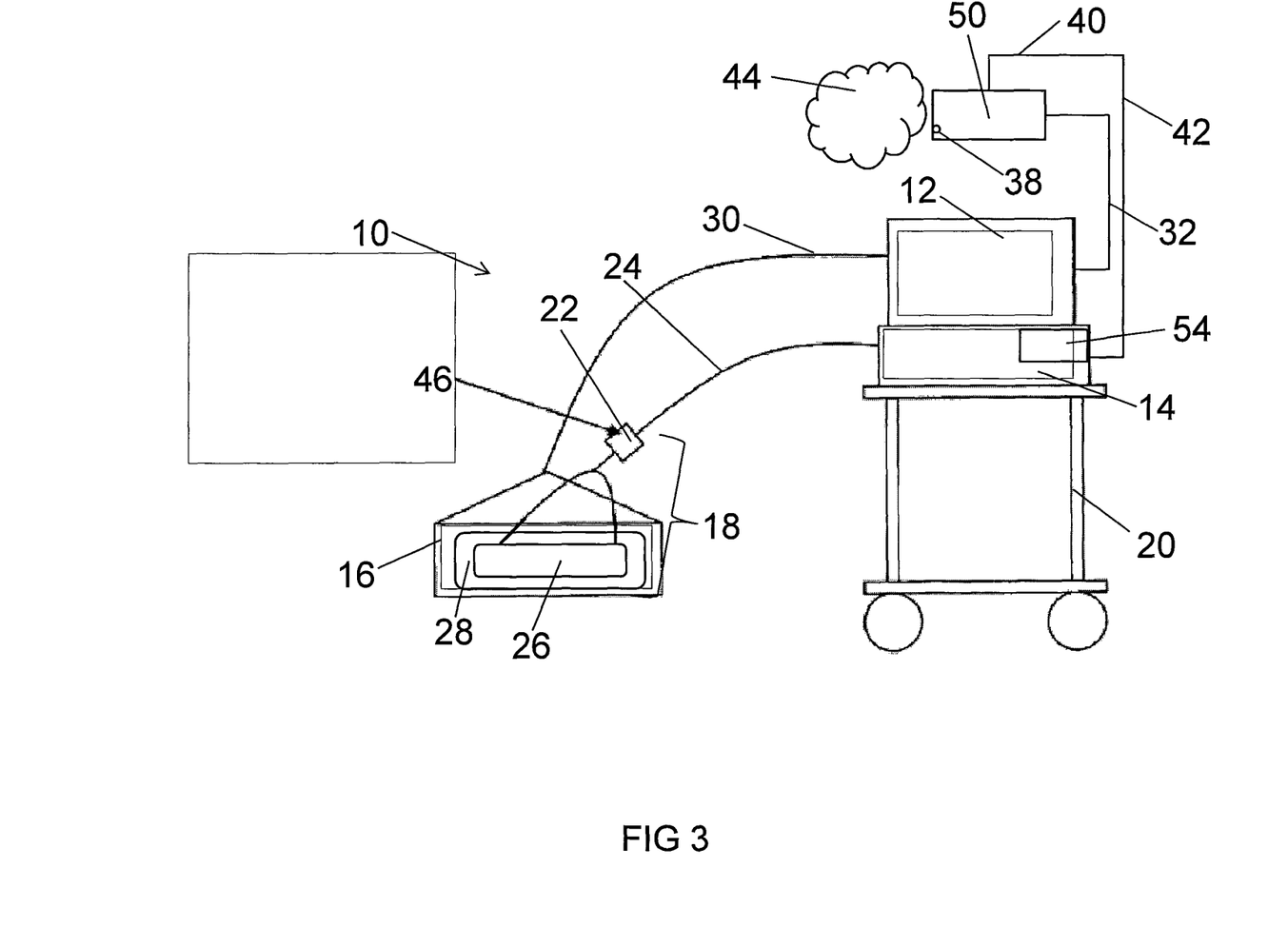
FIG. 3 illustrates a schematic view of a third embodiment of a surgical device.
Figure 4:
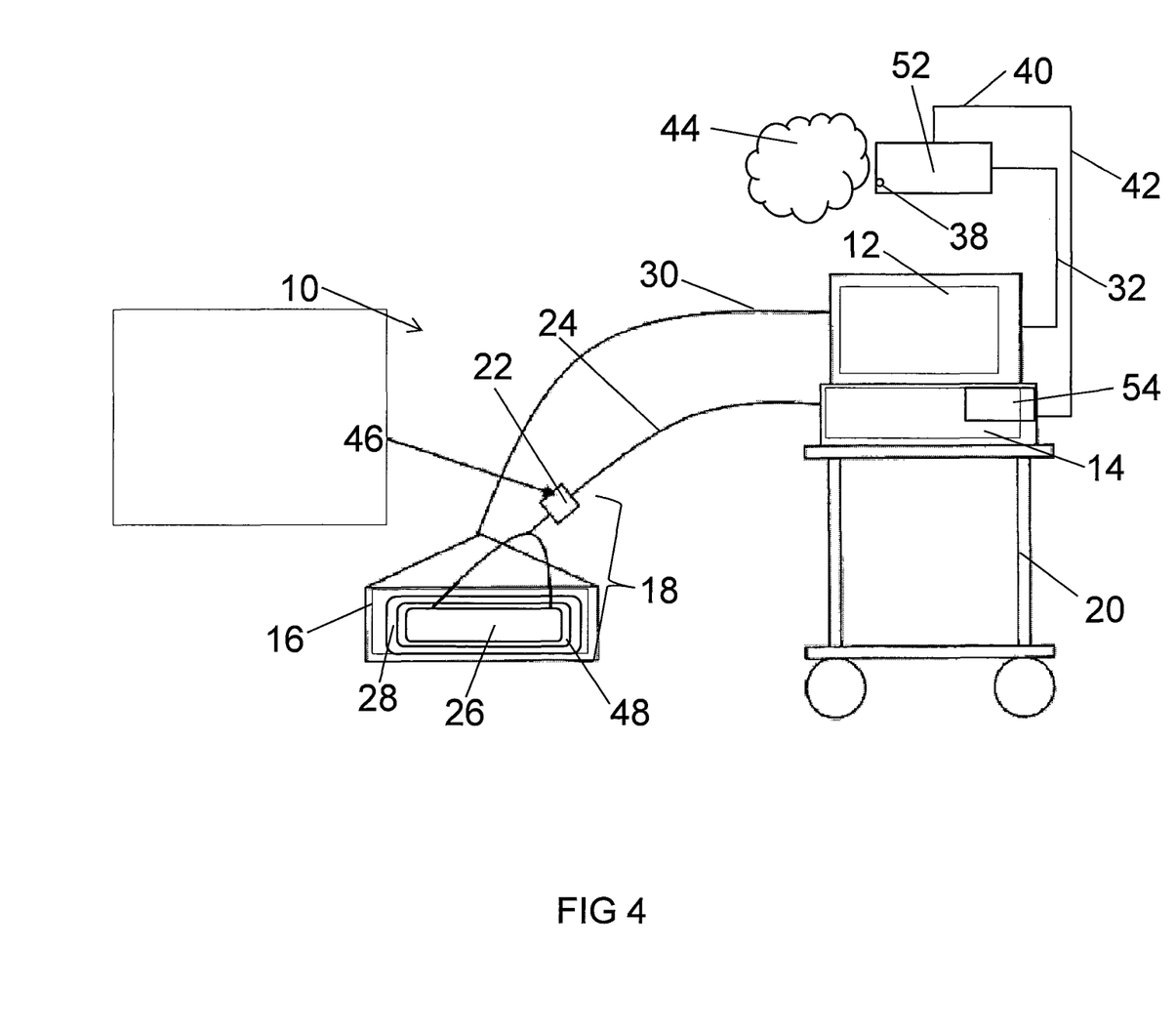
FIG. 4 illustrates a schematic view of a fourth embodiment of a surgical device.

Optionally the user of the surgical device 10 can also not place a foot onto the measuring electrode 26a and 26b and instead place a foot between the measuring electrode 26a and 26b. Thus the user can actuate the foot switch 16 in order to activate the surgical generator 12 without activating the smoke-gas extraction device 14. Alternatively the measuring electrode 26a and 26b can be formed so that they jointly extend over the entire surface of the foot switch 16. In this case activating the foot switch 16 upon or directly before activating the surgical generator 12 leads to an automatic activation of the smoke-gas extraction device 14. In an alternative embodiment only one measuring electrode 26 can be used, in particular a measuring electrode 26a that essentially extends over an entire surface of the foot switch 16 (c.f. FIG. 3 and FIG. 4).

An electrosurgical instrument 34 is connected in this embodiment to the surgical generator 12 by an electric conduit 32. The electrosurgical instrument 34 can form a part of the surgical device 10 or can be connected with the surgical device 10. The electrosurgical instrument 34 has electrodes 36 which are used for cutting and coagulating and which can be supplied by the surgical generator 12 with a high frequency alternating voltage. The electrosurgical instrument 34 additionally includes an opening 38 which is connected with a lumen 40 of a conduit 42. The conduit 42 is connected with the smoke-gas extraction device 14 so that the smoke-gas extraction device 14 can extract smoke-gas 44 through the opening 38 and the lumen 40 wherein the smoke-gas has be generated during cutting and/or coagulating of tissue with the electrosurgical instrument 34.

The surgical generator 12 is configured to provide energy for an energy based surgical instrument, in this embodiment for the electrosurgical instrument 34. As an alternative to the electrosurgical instrument 34 also another energy based surgical instrument can be connected to the surgical generator 12 and supplied with energy by the surgical generator 12. An ultrasound surgical instrument 50 (c.f. FIG. 3) or a laser surgical instrument 52 (c.f. FIG. 4) are suitable as alternatively connect able energy based surgical instruments.

The smoke-gas extraction device 14 is configured to extract the smoke-gas 44. For this purpose the smoke-gas extraction device 14 has a smoke-gas extraction pump 54 which sucks the smoke-gas 44 through the opening 38 and the lumen 40 of the conduit 42 into the smoke-gas extraction device 14 so that the smoke-gas is removed from the environment, in particular from the tissue to be treated. This facilitates improving the visibility of the tissue to be treated.

The surgical device 10 does not place any requirements upon the compatibility of the surgical generator 12, the electrosurgical instrument 34 or the foot switch for the smoke-gas extraction device 14. The capacitive sensor 18 and the smoke-gas extraction device 14 can thus be connected with suitable known surgical devices. This facilitates the retrofitting suitable known surgical devices.

Figure 5:
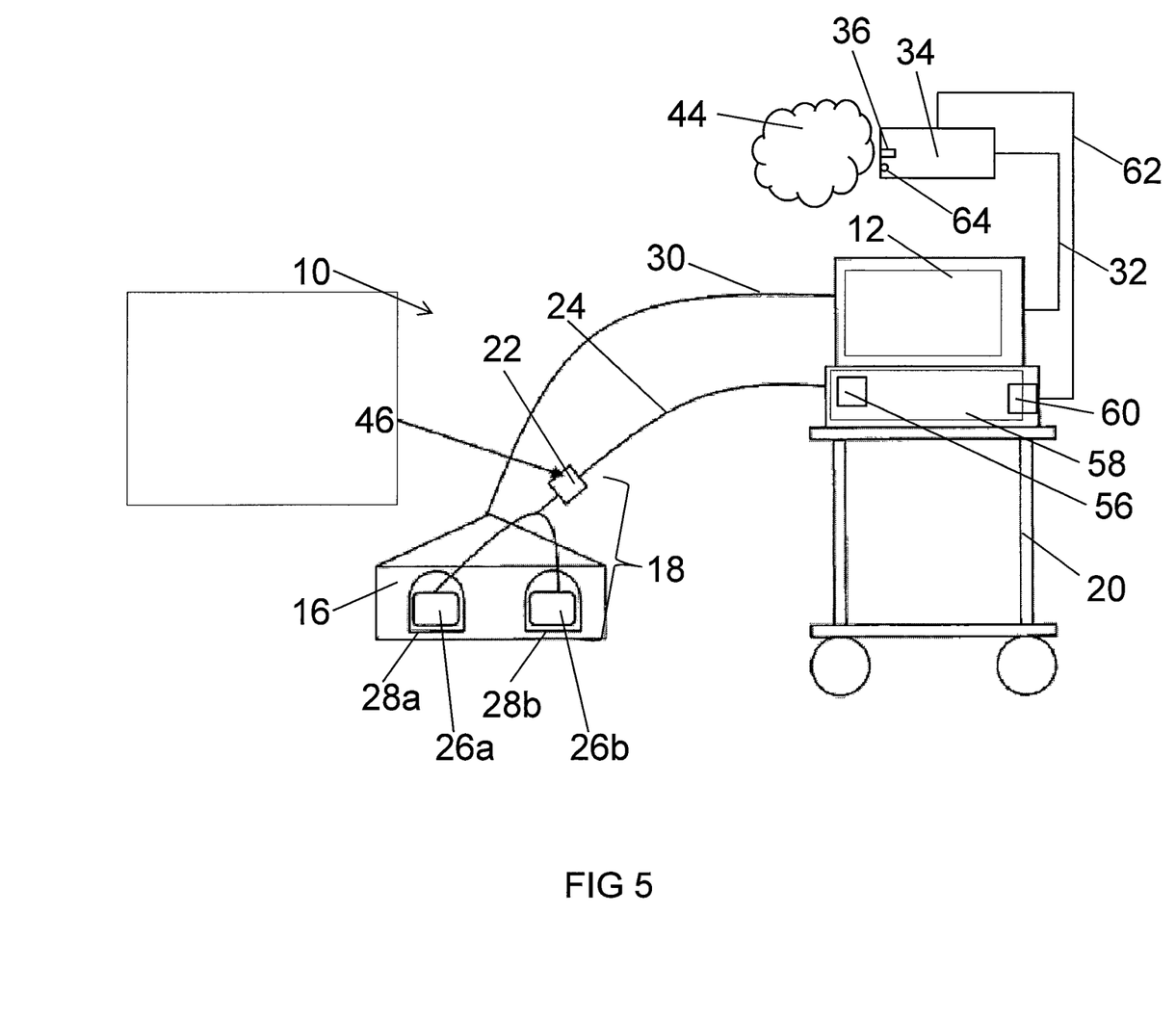
FIG. 5 illustrates a schematic view of a fifth embodiment of a surgical device.

Instead of the smoke-gas extraction device 14 the surgical device 10 can also have another functional device or plural functional devices. For example a blinking light 56, an illumination device 58 (c.f. FIG. 5), a control for a charger, a video recording device an audio recording device, a temperature control device or for example also a control unit for other external devices such as e.g. a pump for coolant supply or a computer or a mobile telephone, a tablet computer or similar.

Figure 2:
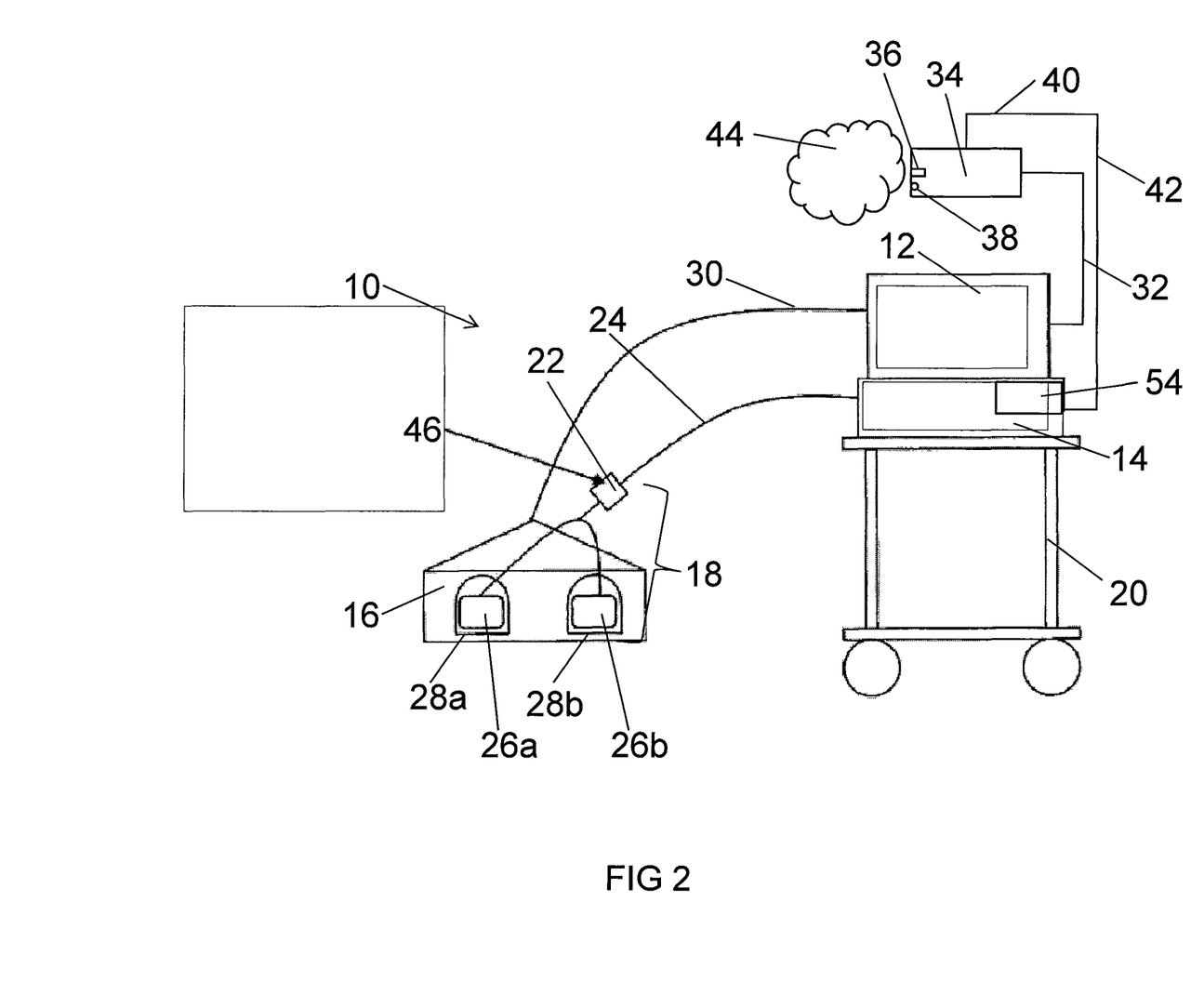
FIG. 2 illustrates a schematic view of a second embodiment of a surgical device.

FIG. 2 illustrates a second embodiment of the surgical device 10. The second embodiment is essentially identical to the first embodiment. Contrary the first embodiment however the measuring electronics 22 in the second embodiment of the surgical device 10 are not arranged in the smoke-gas extraction device 14 but in a measuring electronics housing 46. The measuring electronics housing 46 is arranged between the measuring electrodes 26a and 26b and the smoke-gas extraction device 14 at the sensor cable 24. This facilitates arranging the measuring electronics 22 proximal to the measuring electrodes 26a and 26b in order to reduce interferences.

In this embodiment the foils 28a and 28b are disposable foils and the sensor cable 24 with the measuring electronics housing 46 is reuse able. Alternatively also the foils 28a and 28b can be reuse able or the sensor cable 24 can be a disposable cable that is provided for one time use.

The function of the second embodiment of the surgical device 10 is essentially identical to the function of the first embodiment. Also in the second embodiment of the surgical device 10 the surgical device 10 has a functional device configured as a smoke-gas extraction device 14.

FIG. 3 illustrates a third embodiment of the surgical device 10. The third embodiment is essentially identical to the second embodiment. Contrary to the second embodiment however the third embodiment includes an ultrasound surgical instrument 50 that is connected to the surgical generator 12. The ultrasound generator 50 uses ultrasonic waves for cutting tissue. Furthermore a single measuring electrodes 26 and foil 28 is glued onto the foot switch 16 instead of two measuring electrodes 26a and 26b. The measuring electrode 26 covers almost an entire surface of the foot switch 16.

The function of the third embodiment of the surgical device 10 is essentially identical to the function of the first embodiment. Also in the third embodiment of the surgical device 10 the surgical device 10 has a functional device configured as a smoke-gas extraction device 14.

FIG. 4 illustrates a fourth embodiment of the surgical device 10. The fourth embodiment is essentially identical to the third embodiment. Contrary to the third embodiment however the fourth embodiment includes a laser surgical instrument 52 that is connected to the surgical generator 12. The laser surgical instrument uses laser beams for cutting and/or coagulating tissue. Furthermore a shield electrode 48 is arranged on the foil 28 about the measuring electrode 26. The shield electrode 48 is used for shielding an in homogenous edge portion of the electrical field from the measuring electrodes 26.

Also the function of the fourth embodiment of the surgical device 10 is essentially identical to the function of the first embodiment. Also in the fourth embodiment of the surgical device 10 the surgical device 10 has a functional device configured as a smoke-gas extraction device 14.

FIG. 5 illustrates a fifth embodiment of the surgical device 10. The fifth embodiment is essentially identical to the second embodiment. Contrary to the second embodiment however the surgical device 10 in the fifth embodiment includes a blinking light 56 and an illumination device 58 instead of the smoke-gas extraction device 14. These are connected with the measuring electronics 22 of the capacitive sensor 18. Thus in this case the functional device is an illumination device 58 which additionally includes the blinking light 56. The capacitive sensor 18 first activates the blinking light 56 in this embodiment and thereafter the illumination device 58. Alternatively the blinking light 56 and the illumination device 58 can also be activated synchronously.

The blinking light 56 is used for warning the user of the surgical device 10 when the illumination device 58 is activated. Furthermore the blinking light 56 is also used as a warning for the activation of the surgical generator 12 and thus the activation of the electrosurgical instrument 34. When a synchronous activation of the blinking light 56 and the illumination device 58 is performed the blinking light 56 provides a status display for the activated state of the illumination device 58.

The illumination device 58 has a light source 60 and is connected through the conduit 62 with an outlet opening 64 of the electrosurgical instrument 34. The light source 60 of the illumination device 58 provides a special light which is provided through the conduit 62 to the outlet opening 64 in order to illuminate the tissue to be treated when the electrosurgical instrument 34 is used. This facilitates improving visibility of the tissue to be treated. Alternatively a light source for providing the special light can also be arranged in the electrosurgical instrument 34 and the illumination device 58 can be used to supply the light source with energy.

The function of the fifth embodiment of the surgical device 10 is similar to the function of the first embodiment and differs essentially in that the functional device in this case is not a smoke-gas extraction device 14 but an illumination device 58 with a signal light 56.

Figure 6:
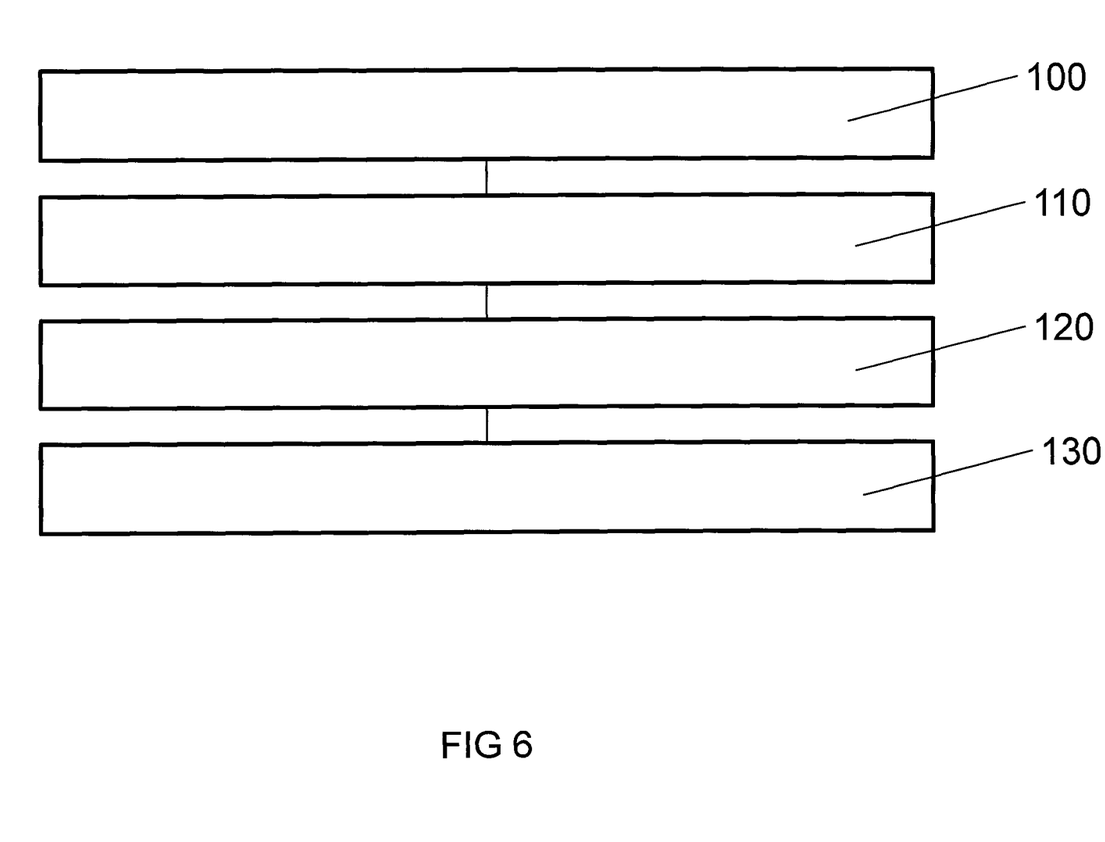
FIG. 6 illustrates a block diagram of an embodiment of a method for essentially synchronous automatic activating and deactivating of a functional device in the form of a smoke-gas extraction device and a surgical generator of a surgical device.

FIG. 6 illustrates a block diagram of a method for essentially synchronous automatic activating and deactivating of a function device configured as a smoke-gas extraction device and a surgical generator of a surgical device. The surgical device includes a switch for activating and deactivating the surgical generator and a measuring electrode of a capacitive sensor arranged at the switch for activating and deactivating the smoke-gas extraction device. The method includes the following steps:

100 placing an object onto the measuring electrode of the capacitive sensor.

110 measuring a capacity change at the measuring electrode through the capacitive sensor. Alternatively or in addition thereto a capacity at the measuring electrode can also be measured.

120 automatic activating or automatic deactivating of the smoke-gas extraction device when a predetermined threshold value of a capacity change is exceeded. Alternatively or additionally the smoke-gas extraction device can also be activated automatically or deactivated automatically when a predetermined threshold value of a capacity is exceeded or undercut. In case both, a capacity change and a capacity, are measured and a predetermined threshold value is provided for both, the automatic activation and automatic deactivation of the smoke-gas extraction device can also be a function of exceeding or undercutting both threshold values.

130 actuating the switch for activating the surgical generator or removing the object from the switch for deactivating the surgical generator.

In this embodiment of the method the threshold value of the capacity change is selected so that the smoke-gas extraction device is activated automatically when the switch is actuated and automatically deactivated when the object is removed from the capacitive sensor. This assures that essentially synchronous automatic activating and deactivating of the surgical generator and the smoke-gas extraction device is performed. Alternatively or additionally the threshold value of the capacity can be selected so that the smoke-gas extraction device is activated when the switch is activated and deactivated when the object is removed from the capacitive sensor.

Additionally the threshold value can be alternatively adjusted so that the smoke-gas extraction device is already activated before actuating the switch, for example when an object is moved close to the measuring electrode of the capacitive sensor. This facilitates activating the smoke-gas extraction device without activating the surgical generator.

The method can be performed alternatively also with another or plural other functional devices. For example the functional device can be provided as a blinking light, an illumination device, a control for a charger, a video recording device, an audio recording device, a temperature control device or for example also a control device for additional devices such as e.g. a pump for coolant supply or a computer, a mobile telephone, a tablet computer or similar.

REFERENCE NUMERALS AND DESIGNATIONS 10 surgical device
12 surgical generator
14 smoke-gas extraction device
16 foot switch
18 capacitive sensor
20 transport cart
22 measuring electronics
24 sensor cable
26, 26a, 26b measuring electrode
28, 28a, 28b foil
30 switch cable
32 electrical conductor
34 electrosurgical instrument
36 electrode
38 opening
40 lumen
42 conduit
44 smoke-gas
46 housing
48 shielding electrode
50 ultrasound surgical instrument
52 laser surgical instrument
54 smoke-gas extraction pump
56 blinking light
58 illumination device
60 light source
62 conduit
64 outlet opening

The invention claimed is:

1. A surgical device, comprising:
a surgical generator configured to provide energy for an energy based surgical instrument;
a functional device configured to provide a function in its activated state;
a first switch for activating and deactivating the surgical generator; and
a second switch in a form of a capacitive sensor including at least one measuring electrode that is arranged on the first switch,
wherein:
the surgical generator and the functional device are configured to be separately activated and deactivated by actuation of the first switch and the second switch, respectively;
the capacitive sensor is configured to measure a capacity change or a capacity at the at least one measuring electrode and activate or deactivate the functional device as a function of a measured capacity change or capacity such that initially the functional device and immediately thereafter or synchronously the surgical generator is activated when the first switch is actuated on which the at least one measuring electrode of the capacitive sensor is arranged; and
the capacitive sensor is a contact sensor or a proximity sensor that is configured to activate the functional device, when a hand, a foot, or an object approaches or touches the first switch.

2. The surgical device according to claim 1, wherein the capacitive sensor is configured such that activating the surgical generator by actuating the first switch also causes the capacitive sensor to measure a capacity change or a capacity at the at least one measuring electrode and to activate the functional device.

3. The surgical device according to claim 1, wherein the capacitive sensor is configured such that deactivating the functional device also causes deactivating the surgical generator by the first switch.

4. The surgical device according to claim 1, wherein the capacitive sensor is configured so that activating or deactivating the functional device is performed synchronously with activating or deactivating the surgical generator when the first switch is actuated.

5. The surgical device according to claim 1, further comprising a capacitive measuring device that is attachable at the first switch, wherein the capacitive measuring device includes the at least one measuring electrode of the capacitive sensor.

6. The surgical device according to claim 1, wherein the capacitive sensor includes measuring electronics configured to measure the capacity change or the capacity at the at least one measuring electrode.

7. The surgical device according to claim 6, wherein the measuring electronics of the capacitive sensor are arranged in the functional device.

8. The surgical device according to claim 6, wherein the capacitive sensor is connected with the functional device through a cable and the measuring electronics of the capacitive sensor are arranged at the cable between the at least one measuring electrode and the functional device.

9. The surgical device according to claim 1, wherein the capacitive sensor includes at least one shielding electrode which is arranged proximal to the at least one measuring electrode and configured to shield in a non-homogenous edge portion of an electrical field of the at least one measuring electrode.

10. The surgical device according to claim 1, wherein the first switch is a foot switch that is configured to be actuated by a foot or by plural feet.

11. The surgical device according to claim 1, further comprising an energy based surgical instrument, wherein the energy based surgical instrument is configured to cut and/or coagulate tissue, and the energy based surgical instrument is:
an ultrasound surgical instrument,
a laser surgical instrument, or
an electrosurgical instrument that includes at least one electrode and is configured to be operated by a high frequency alternating voltage to cut, and/or coagulate tissue.

12. The surgical device according to claim 1, wherein the second switch is arranged on a surface of the first switch.

13. The surgical device according to claim 1, wherein the functional device is a smoke-gas extraction device.

* * * * *